United States Patent
Kim et al.

(10) Patent No.: US 10,174,312 B2
(45) Date of Patent: Jan. 8, 2019

(54) SCREENING METHOD FOR DRUG TARGET GENE USING HETEROZYGOUS DELETION FISSION YEAST STRAIN

(71) Applicant: Korea Research Institute of Bioscience and Biotechnology, Daejeon (KR)

(72) Inventors: Dong-Uk Kim, Daejeon (KR); Kwang-Lae Hoe, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 403 days.

(21) Appl. No.: 14/728,789

(22) Filed: Jun. 2, 2015

(65) Prior Publication Data
US 2015/0344874 A1 Dec. 3, 2015

(30) Foreign Application Priority Data
Jun. 3, 2014 (KR) .................. 10-2014-0067556

(51) Int. Cl.
*C12N 15/10* (2006.01)
*C12Q 1/02* (2006.01)

(52) U.S. Cl.
CPC ..... *C12N 15/1079* (2013.01); *C12N 15/1065* (2013.01); *C12Q 1/025* (2013.01)

(58) Field of Classification Search
None
See application file for complete search history.

(56) References Cited

U.S. PATENT DOCUMENTS

| | | | |
|---|---|---|---|
| 9,670,480 B2* | 6/2017 | Hoe | C12N 15/1034 |
| 2002/0115140 A1* | 8/2002 | Levinson | C07K 14/4702 435/69.1 |
| 2004/0009494 A1* | 1/2004 | Murray | C12Q 1/48 435/6.16 |
| 2004/0265861 A1* | 12/2004 | Goldfarb | C12N 15/1079 435/6.1 |
| 2007/0128605 A1* | 6/2007 | Yang | C12N 9/1029 506/14 |

FOREIGN PATENT DOCUMENTS

| | | |
|---|---|---|
| KR | 10-2003-0086216 | 12/2002 |
| KR | 10-2009-0111695 | 4/2008 |

OTHER PUBLICATIONS

Cheuk Hei Ho Dissertation entitled "Molecular barcoded plasmid yeast ORF library: linking bioactive compounds to their cellular targets and mapping dosage suppressor networks" (Dept of Molecular Genetics, University of Toronto, 2011).*
Xu et al in "Genome-wide fitness test and mechanism-of-action studies of inhibitory compounds in Candida albicans" (PLOS ONE).*
Ma et al in "Genome-Wide Screening for Genes Associated with FK506 Sensitivity in Fission Yeast" (Plos ONE).*
Simon in "Yeast as a model system for anticancer drug discovery" (2001: Emerging Therapeutic Targets, vol. 5, No. 2, pp. 177-195).*
Zhang et al "Genome-Wide Screening for Genes Associated with Valproic Acid Sensitivity" PloS ONE vol. 8, No. 7, Jul. 5, 2013, pp. 1-11.*
Giaever & Nislow in "The Yeast Deletion Collection: A Decade of Functional Genomics" (Genetics, vol. 197, pp. 451-465, published Jun. 1, 2014). (Year: 2014).*
Kim et al. (2010) "Analysis of a Genome-Wide Set of Gene Deletions in the Fission Yeast *Schizosaccharomyces pombe*", Nat. Biotechnol. 28:617-623.
Pierce et al. (2006) "A Unique and Universal Molecular Barcode Array", Nat. Methods 3:601-603.
Kapitzky et al., "*Cross-species chemogenomic profiling reveals evolutionarily conserved drug mode of action*", Mol. Syst. Biol., 2010, 6:451.

* cited by examiner

*Primary Examiner* — Catherine S Hibbert
(74) *Attorney, Agent, or Firm* — Leydig, Voit & Mayer, Ltd.

(57) ABSTRACT

The present invention relates to a screening method for a drug target gene by using chemical-genetic profile compendium of the heterozygous deletion fission yeast strain and the comparative genetic analysis using the same. More precisely, the present inventors constructed the chemical-genetic profile compendium for drug candidates from the heterozygous deletion fission yeast strain of *Schizosaccharomyces pombe* (*S. pombe*), and then compared with the compendium with the chemical-genetic profile compendium of the budding yeast *Saccharomyces cerevisiae* (*S. cerevisiae*) in order to select efficiently drug target genes showing drug sensitivity. The screening method of the present invention can be efficiently used for the identification of a drug target gene in various eukaryotes because it facilitates the selection of a drug target gene showing sensitivity to the drug from the chemical-genetic profile compendium of the heterozygous deletion fission yeast strain.

3 Claims, 9 Drawing Sheets
Specification includes a Sequence Listing.

| Num | S. pombe | S. cerevisiae (2004) | S. cerevisiae (2008) |
|---|---|---|---|
| 1 | 5-Fluorouracil | 5-Fluorouracil | 5-fluorouracil |
| 2 | Actinomycin D | Actinomycin D | |
| 3 | Brefeldin A | | Brefeldin A |
| 4 | Clotrimazole | Clotrimazole | Clotrimazole |
| 5 | Camptothecin | Camptothecin | Camptothecin |

• • •

| 45 | Terbinafine | Terbinafine | Terbinafine |
|---|---|---|---|
| 46 | Tunicamycin | Tunicamycin | Tunicamycin |
| 47 | Valproic acid | Valproic Acid | |

Drugs tested in both yeasts : 36

*Finding ecDTs by orthologous mapping*

Drugs with ecDT: 13

*Filtering out ecDTs with no essentiality, multi-drug sensitivity, and low mammalian homology*

Drugs with ecDT: 9

Figure 7

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: CPN1

<400> SEQUENCE: 1
cgtctgtgag gggagcgttt                                                    20

<210> SEQ ID NO 2
<211> LENGTH: 25
<212> TYPE: DNA
<213> ORGANISM: Artificial
<220> FEATURE:
<223> OTHER INFORMATION: CPN10

<400> SEQUENCE: 2
gatgtgagaa ctgtatccta gcaag                                              25

<210> SEQ ID NO 3
<211> LENGTH: 22
<212> TYPE: DNA
<213> ORGANISM: Artificial
<220> FEATURE:
<223> OTHER INFORMATION: CPC1

<400> SEQUENCE: 3
tgattttgat gacgagcgta at                                                 22

<210> SEQ ID NO 4
<211> LENGTH: 25
<212> TYPE: DNA
<213> ORGANISM: Artificial
<220> FEATURE:
<223> OTHER INFORMATION: CPC3

<400> SEQUENCE: 4
ggctggcctg ttgaacaagt ctgga                                              25

SCREENING METHOD FOR DRUG TARGET GENE USING HETEROZYGOUS DELETION FISSION YEAST STRAIN

BACKGROUND OF THE INVENTION

1. Field of the Invention

The present invention relates to a screening method for a drug target gene using chemical-genetic profile compendium of the heterozygous deletion fission yeast strain and the comparative genetic analysis using the same.

2. Description of the Related Art

According to the increasing interest in the quality of life due to the world-wide aging and the welfare society possibly made by the increase of general income of the people, the demand for medicine has been continually increased domestically and internationally likewise. Chronic diseases and new diseases are threatening human health these days. But, as basic science technology including bio-engineering techniques advances, studies on the diseases progress greatly, based on which the development of new medicine has also been advanced rapidly.

To develop a new drug, techniques of combinatorial chemistry and functional genomics have been used. Combinatorial chemistry technique is the method for screening an already known drug target through a library of organic-chemically synthesized compounds. In the method of functional genomics, animal cells or target cells are treated with a specific drug, which are then compared with the non-treated group by using DNA chip to identify a gene whose expression has been changed by that, in order to search a gene group related to disease or displaying a pharmaceutical effect. By taking advantage of the functional genomics technique, a mechanism responding to a drug and a target gene can be predicted, so that the acting point of the drug can be easily identified. The time and costs for the development of a new drug can also be saved and a cause of side effect can also be notified, enabling the prevention of it. However, this method has a disadvantage as well, which is it costs high expenses and requires more study to search a target gene.

In the meantime, the method of "chemical-genetic profiles" indicates the in vivo screening method to search a gene involved in the activation of a drug in cells by observing the changes of phenotype caused by genetic deletion based on the functional genomics after the cells have been treated with a specific drug. More precisely, changes of the sensitivity of heterozygous mutant to the specific drug are measured herein, by which almost every target gene can be easily identified. So, this method is useful for the screening of a target gene particularly in relation to a specific drug, a toxin, and a natural mixture.

In the method of chemical-genetic profiles, the genome-wide chemical-genetic profiles obtained from the deletion library of budding yeast like *Saccharomyces cerevisiae* (*S. cerevisiae*) are very useful for the identification of the unknown mode-of-action of a drug. In general, genome-deletion strain profiles facilitate the screening of a drug target gene or protein by screening a gene displaying a change in expression pattern by high-throughput spot assay (A. M. Smith et al., Pharmacol. Ther. 127 (2010) 156-164, A. B. Parsons et al., Nat. Biotechnol. 22 (2004) 62-69) and DNA-chip after treating target cells with a specific drug.

It has been reported that the success rate of target gene screening was increased to 70% from the previous rate of 25% when the screening of a target gene was performed with 80 conventional drugs by using the constructed budding yeast library (Lum P Y et. al., Cell. 2004; 116(1):121-137).

According to the previous report, the principal of gene screening was based on drug-induced haploinsufficiency (DI-HI), that is the screening was achieved by measuring the reduction of such a gene that induced growth defect in the presence of the drug. According to the previous report, approximately 3% (180 genes) of the total 6,000 genes of a budding yeast displayed drug-induced haploinsufficiency even under normal culture condition (Deutschbauer et al., Genetics, 169 (2005), 1915-1925).

*Schizosaccharomyces pombe* (*S. pombe*) is a fission yeast, which belongs to ascomycetes like the budding yeast *S. cerevisiae*, but is not so closely related to *S. cerevisiae* in the evolutionary aspect. *S. pombe* (Wood V. et al., Nature. 45:871-880, 2002) is the $6^{th}$ microorganism among the eukaryotes whose nucleotide sequence has been completely sequenced after *S. cerevisiae* (Goffeau A. et al., Science, 274:546-567, 1996). According to the sequencing result, *S. pombe* has the most efficient chromosome structure with less functional repeats, among the eukaryotes whose nucleotide sequence has been identified, and has the least protein determining genes, 4,824. However, 43% of the genes of *S. pombe* are known to contain intron. In addition, in *S. pombe*, such genes that are important in relation to cell cycle regulation, proteolysis, protein phosphorylation, and RNA splicing are well preserved. 31% of the genes of *S. pombe* are different from the genes of *S. cerevisiae*, and they are rather closer to those of human. Therefore, it is considered to be an efficient method to study the functions of *S. pombe* genes with comparing the genes of *S. cerevisiae* in order to understand the functions of human genes better.

Regarding the heterozygous deletion strain and the library thereof used for the chemical-genetic profiles, Korean Patent No. 10-0475645 describes method for screening of drug using systematic deletion mutant of fission yeast, and Korean Patent No 10-1098032 describes genome-wide construction of *Schizosaccharomyces pombe* heterozygous deletion mutants containing gene-specific barcodes by the methods of 4-round serial or block PCR, or total gene synthesis thereof.

Therefore, the present inventors tried to develop an efficient method for screening a drug target gene useful for the development of a new drug. As a result, the present inventors established the chemical-genetic profile compendiums of candidate drugs from the library of *S. pombe* heterozygous deletion fission yeast strain, and compared the profile compendiums with those of *S. cerevisiae*, the budding yeast, to select a drug target gene displaying sensitivity to the drug. At last, the present inventors completed this invention by confirming that the method for screening the gene targeting drug using the heterozygous deletion fission yeast strain of the invention could be efficiently used for the identification of a drug target gene in various eukaryotes.

PRIOR ARE REFERENCES

Patent References (patent reference 1) Korean Patent No. 10-0475645
(patent reference 2) Korean Patent No. 10-1098032

Non-Patent References (non-patent reference 1) D. U. Kim, J. Hayles, D. Kim, et al., Analysis of a genome-wide set of gene deletions in the fission yeast *Schizosaccharomyces pombe*, Nat. Biotechnol. 28 (2010) 617-623.

(non-patent reference 2) S. E. Pierce, E. L. Fung, D. F. Jaramillo, et al., A unique and universal molecular barcode array, Nat. Methods 3 (2006) 601.603.

SUMMARY OF THE INVENTION

It is an object of the present invention to provide a screening method for a drug target gene by using chemical-genetic profile compendium of heterozygous deletion fission yeast strain and the comparative genetic analysis using the same.

To achieve the above object, the present invention provides a screening method for a drug target gene comprising the following steps:

i) culturing each of the heterozygous deletion strain library of *Schizosaccharomyces pombe* (*S. pombe*) and *Saccharomyces cerevisiae* (*S. cerevisiae*);

ii) treating the culture medium of step i) with a sample drug, followed by further culture;

iii) confirming the growth of the strain library cultured in step ii); and iv) comparing the compendium of heterozygous deletion genes of the *S. pombe* strain library demonstrating the inhibition of growth with the compendium of heterozygous deletion genes of the *S. cerevisiae* strain library.

The present invention also provides a screening method for a drug target gene comprising the following steps:

i) culturing *S. pombe* heterozygous deletion strain library;

ii) treating the culture medium of step i) with a sample drug, followed by further culture;

iii) confirming the growth of the strain library cultured in step ii); and iv) confirming the compendium of heterozygous deletion genes of the *S. pombe* strain library demonstrating the inhibition of growth in step iii).

ADVANTAGEOUS EFFECT

The screening method of the present invention can be efficiently used for the identification of a drug target gene in various eukaryotes because it facilitates the selection of a drug target gene showing sensitivity to the drug from the chemical-genetic profile compendium of the heterozygous deletion fission yeast strain.

BRIEF DESCRIPTION OF THE DRAWINGS

The application of the preferred embodiments of the present invention is best understood with reference to the accompanying drawings, wherein:

FIG. 7 is a schematic diagram illustrating the selection of ecDTs from the *S. pombe* compendiums and *S. cerevisiae* compendiums.

DESCRIPTION OF THE PREFERRED EMBODIMENTS

Figure 1:
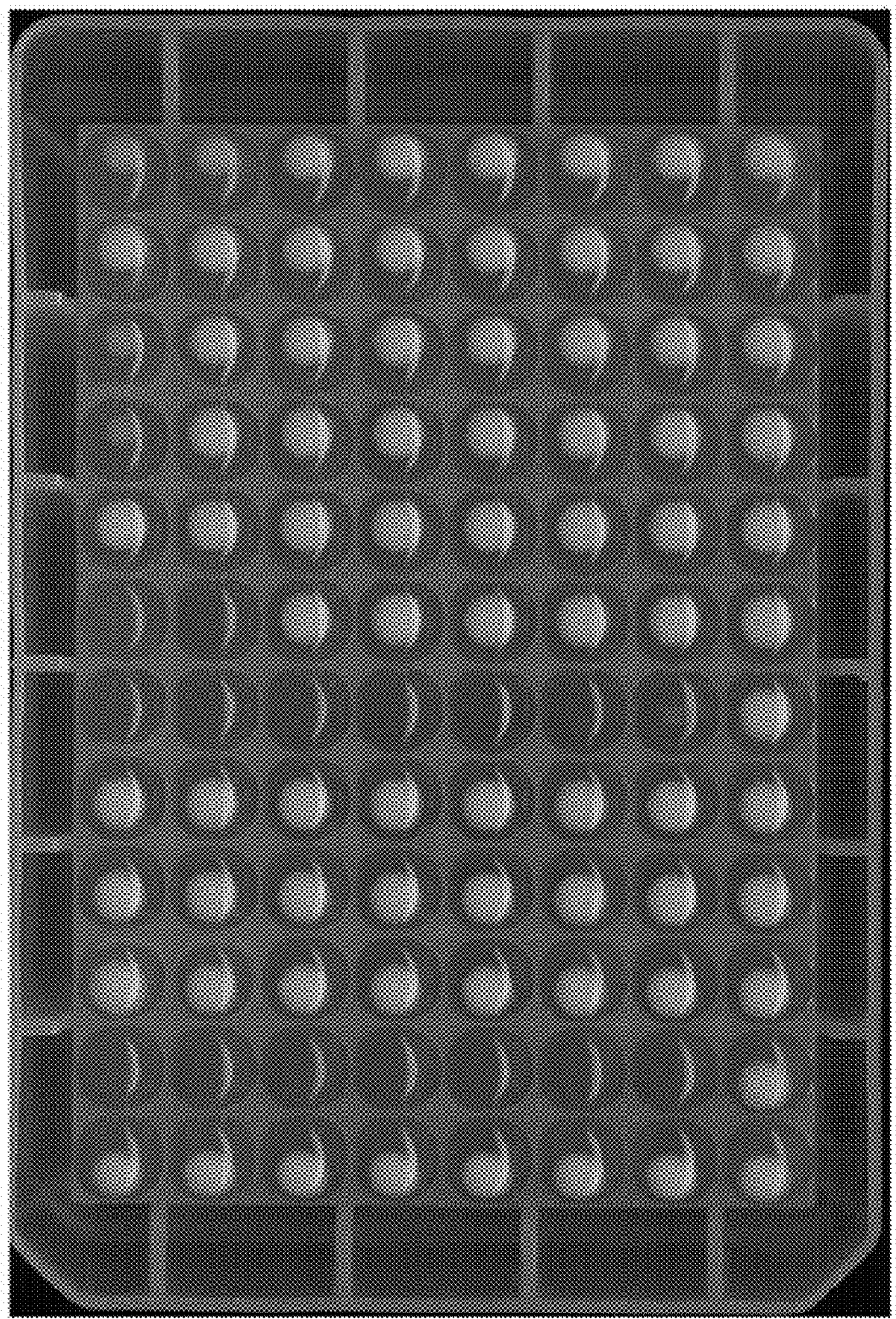
FIG. 1 is a diagram illustrating the pooled growth in a 48-well plate in order to determine the optimum dose of the target drug. The drug diluted in 7 steps serially was treated to each row and total 12 different drugs were treated according to the order of line.

Hereinafter, the terms used in this invention are defined.

The term "chemical-genetic profiles" of the invention indicates a method for screening a gene involved in intracellular drug mechanism by observing the changes of phenotype caused by genetic deletion based on the functional genomics after the cells have been treated with a specific drug. The word "chemical" in the term "chemical-genetic profiles" indicates a drug, a bioactive compound, or a natural extract approved by FDA. The word "genetic" in the term 'chemical-genetic profiles' indicates the library of genome-wide deletion strains. The word "profile" in the term "chemical-genetic profiles" indicates the quantitative confirmation of growth defect displayed in the library strains.

The term "haploinsufficiency (HI)" in this invention indicates the phenomenon of the reduction of a gene product that displays an abnormal phenotype such as growth defect in a living subject under the normal condition. The haploinsufficiency results in abnormal growth or causes disease because a gene, when only one functional copy of a diploid organism gene is conserved and the other copy is inactive due to the mutation, loses its function and accordingly cannot produce as many gene products as the wild-type can produce under this condition.

The term "drug-induced haploinsufficiency" in this invention indicates the phenomenon that displays an abnormal phenotype such as growth defect when the diploid gene of a living subject is affected by a drug and thus the expression of the gene production is reduced.

The term "orthologous gene" of the invention indicates the homolog gene observed in two or more species, which shares evolutionarily the same origin in the speciation process. The orthologous genes among the basic species display high sequence homology and have similar protein structures, based on which equal biological functions are expected.

Regarding the term "evolutionarily conserved drug targets (ecDTs)" of the invention, when two yeast heterozygous deletion strains to the orthologous gene of the *S. pombe* and *S. cerevisiae* strain chemical-genetic profiles are sensitive to a given drug, the orthologous gene is defined as ecDT. This definition is attributed to the continually observed similarity in functions between the two yeasts, suggesting that ecDT is directly affected by the given drug. Besides, ecDT is applied not only to these two yeasts but also to eukaryotic cells.

Hereinafter, the present invention is described in detail.

The present invention provides a screening method for a drug target gene comprising the following steps:

i) culturing each of the heterozygous deletion strain library of *Schizosaccharomyces pombe* (*S. pombe*) and *Saccharomyces cerevisiae* (*S. cerevisiae*);

ii) treating the culture medium of step i) with a sample drug, followed by further culture;

iii) confirming the growth of the strain library cultured in step ii); and iv) comparing the compendium of heterozygous deletion genes of the *S. pombe* strain library demonstrating the inhibition of growth with the compendium of heterozygous deletion genes of the *S. cerevisiae* strain library.

In step i), the said *S. pombe* is a fission yeast which is proliferated by asexual reproduction characterized by binary fission with forming a partition wall in between. In the meantime, the said *S. cerevisiae* is a budding yeast which is reproduced by budding.

In step i), the heterozygous deletion strain is preferably prepared by the method for preparing a gene targeting heterozygous fission yeast strain using a gene targeting deletion cassette comprising a selection marker gene, gene specific microarray barcode sequences arranged on both sides of the selection marker gene, and homologous recombination sites arranged on both sides of the barcode sequence, more preferably by the method described in Korean Patent No. 10-1098032, but not always limited thereto.

The sample drug of step ii) is preferably selected from the group consisting of actinomycin D, brefeldin A, camptothecin, chlorpromazine, cimetidine, clomipramine hydrochloride, clotrimazole, cycloheximide, cytochalasin B, desipramine hydrochloride, dilitiazem hydrochloride, diphenhydramine hydrochloride, dipyridamole, doxorubicin, dyclonine, erythromycin, 5-fluorouracil, fluoxetine hydrochloride (Prozac), fluvastatin sodium salt, gemfibrozil, haloperidol, hydrocortisone, imipramine hydrochloride, indomethacin, methotrexate, metoclopramide hydrochloride, minoxidil, mitomycin C, nicardipine hydrochloride, nifedipine, nitrofurantoin, oligomycin, omeprazole, paromomycin sulfate, phenylbutazone, pramoxine hydrochloride, pravastatin sodium salt, procaine hydrochloride, progesterone, promethazine hydrochloride, sulfamethoxazole, sulfinpyrazone, tamoxifen, terbinafine, theophylline anhydrous, tunicamycin, and valproic acid sodium salt, and more preferably selected from the group consisting of tunicamycin, terbinafine, clotrimazole, doxorubicin, mitomycin C, methotrexate, dyclonine, haloperidol, and erythromycin, but not always limited thereto.

The measurement of the growth in step iii) is preferably performed by DNA chip array or high-throughput spot assay, but not always limited thereto.

In the DNA chip array, the heterozygous deletion strain needs to be constructed in the size of genome; and each deletion strain has to have a specific DNA barcode usable as a molecular probe for the DNA chip; and the DNA microarray chip is preferably customized to be suitable for the measurement of the specific DNA barcode inserted in each strain, for which any commercialized product acceptable in this field can be used (http://pombe.bioneer.co.kr.).

The comparison of each gene compendium in step iv) is to select orthologous genes, but not always limited thereto.

In step iv), the heterozygous deletion gene of the strain library is preferably an evolutionarily conserved Drug Target (ecDT), and the evolutionarily conserved Drug Target has preferably one or more characteristics of the following (i)~(iii);

i) the essential gene necessary for the survival of the strain;

ii) the gene that does not show multi-drug sensitivity (MDS); and iii) the eukaryotic conserved gene.

The drug target gene of *S. pombe* is preferably selected from the group consisting of gpt2, erg1, erg11, vma7, vma1, rpa2, spc7, snf21, cdc10, ssr2, SPCC1450.10c, SPAC22F8.08, rpn12, fet5, and SPAC688.09, but not always limited thereto.

In a preferred embodiment of the present invention, the inventors constructed a *S. pombe* heterozygous deletion strain. To select a drug for this invention and to determine a dose of the drug, the present inventors first selected 47 drug candidates for the investigation of growth inhibition of the heterozygous deletion strain and regarded a dose that demonstrated 0.85<pool fitness (PF)<0.95 as a proper dose for each candidate (see FIGS. 1~4, and Table 2).

To establish *S. pombe* compendium for the drug by using chemical-genetic profile from the *S. pombe* heterozygous deletion strain, the inventors treated *S. pombe* heterozygous deletion strain library with a sample drug, followed by culture. Then, the growth of the strain was confirmed quantitatively by performing DNA chip array. As a result, Z-scores and p-values of the 4400 heterozygous deletion strains treated with 47 drugs were obtained, from which the '*S. pombe* compendium' of the invention was established.

To screen a protein and a gene targeted directly by a specific drug using the *S. pombe* compendium, the inventors performed drug-induced haploinsufficiency (DI-HI) profiling. As a result, it was confirmed that most genes of *S. pombe* were HS and less than 3% of the genes were HI in the aspect of cell growth (see FIG. 5).

In addition, the method of screening through *S. pombe* DIHI profiles to analyze a bioactive compound is limited so that it cannot screen all the drug target proteins directly in various living subjects. Thus, the present inventors screened evolutionarily conserved drug targets (ecDTs) with comparing *S. pombe* compendium and *S. cerevisiae* compendium. As a result of the screening of the evolutionarily conserved Drug Targets (ecDTs) by comparing the compendiums of *S. pombe* and *S. cerevisiae*, 9 drugs which had direct effect on both *S. pombe* and *S. cerevisiae* were selected (see FIGS. 6 and 7). Among the drug target genes which were sensitive particularly to those selected drugs, orthologous genes (see Tables 3 and 4) were identified from the whole length of *S. pombe* genome (see Tables 5 and 6, and FIGS. 8 and 9).

In conclusion, the present inventors prepared the chemical-genetic profile compendium for candidate drugs from the *S. pombe* heterozygous deletion fission yeast strain library. When the prepared compendium was compared with the chemical-genetic profile compendium of *S. cerevisiae*, the drug target genes displaying drug sensitivity were successfully selected. Therefore, the screening method of the present invention can be efficiently used for the identification of a drug target gene in various eukaryotes.

The present invention also provides a screening method for a drug target gene comprising the following steps:

i) culturing *S. pombe* heterozygous deletion strain library;

ii) treating the culture medium of step i) with a sample drug, followed by further culture;

iii) confirming the growth of the strain library cultured in step ii); and iv) confirming the compendium of heterozygous deletion genes of the *S. pombe* strain library demonstrating the inhibition of growth in step iii).

The fission yeast of step i) is an asexually reproducing yeast characterized by binary fission with forming a partition wall in between. This yeast is preferably the one well-informed to those in the art as a fission yeast belonging to *Schizosaccharomyces*, and more preferably *S. pombe*, but not always limited thereto.

The said *S. pombe* of step i) is a fission yeast which is proliferated by asexual reproduction characterized by binary fission with forming a partition wall in between.

In step i), the heterozygous deletion strain is preferably prepared by the method for preparing a gene targeting heterozygous fission yeast strain using a gene targeting deletion cassette comprising a selection marker gene, gene specific microarray barcode sequences arranged on both sides of the selection marker gene, and homologous recombination sites arranged on both sides of the barcode sequence, more preferably by the method described in Korean Patent No. 10-1098032, but not always limited thereto.

The sample drug of step ii) is preferably selected from the group consisting of actinomycin D, brefeldin A, camptothecin, chlorpromazine, cimetidine, clomipramine hydrochloride, clotrimazole, cycloheximide, cytochalasin B, desipramine hydrochloride, dilitiazem hydrochloride, diphenhydramine hydrochloride, dipyridamole, doxorubicin, dyclonine, erythromycin, 5-fluorouracil, fluoxetine hydrochloride (Prozac), fluvastatin sodium salt, gemfibrozil, haloperidol, hydrocortisone, imipramine hydrochloride, indomethacin, methotrexate, metoclopramide hydrochloride, minoxidil, mitomycin C, nicardipine hydrochloride, nifedipine, nitrofurantoin, oligomycin, omeprazole, paromomycin sulfate, phenylbutazone, pramoxine hydrochloride, pravastatin sodium salt, procaine hydrochloride, progesterone, promethazine hydrochloride, sulfamethoxazole, sulfinpyrazone, tamoxifen, terbinafine, theophylline anhydrous, tunicamycin, and valproic acid sodium salt, and more preferably selected from the group consisting of tunicamycin, terbinafine, clotrimazole, doxorubicin, mitomycin C, methotrexate, dyclonine, haloperidol, and erythromycin, but not always limited thereto.

The measurement of the growth in step iii) is preferably performed by DNA chip array or high-throughput spot assay, but not always limited thereto.

In the DNA chip array, the heterozygous deletion strain needs to be constructed in the size of genome; and each deletion strain has to have a specific DNA barcode usable as a molecular probe for the DNA chip; and the DNA microarray chip is preferably customized to be suitable for the measurement of the specific DNA barcode inserted in each strain, for which any commercialized product acceptable in this field can be used (http://pombe.bioneer.co.kr.).

The drug target gene of *S. pombe* is preferably selected from the group consisting of gpt2, erg1, erg11, vma7, vma1, rpa2, spc7, snf21, cdc10, ssr2, SPCC1450.10c, SPAC22F8.08, rpn12, fet5, and SPAC688.09, but not always limited thereto.

The heterozygous deletion gene of the strain library of step iv) is preferably drug-induced haploinsufficiency (DIHI), but not always limited thereto.

In this invention, the present inventors prepared the chemical-genetic profile compendium for the drug candidates from the *S. pombe* heterozygous deletion fission yeast strain library. By comparing the *S. pombe* compendium with the *S. cerevisiae* chemical-genetic profile compendium, a drug target gene displaying drug sensitivity can be effectively selected. Therefore, the screening method of the invention can be efficiently used for the identification of a drug target gene in various eukaryotes.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of *Schizosaccharomyces pombe* (*S. pombe*) Heterozygous Deletion Strain Library <1-1> Construction of Deletion Cassette by Gene Synthesis Method To prepare a *S. pombe* heterozygous deletion strain for the experiment of the present invention, a deletion cassette was first constructed by using the gene synthesis method described in Korean Patent No. 10-1098032, and a gene targeting strain was prepared.

First, the deletion cassette for gene synthesis was designed to be composed of the following three fragments; 1) 5' chromosome homology region and 5' barcode region, 2) kanamycin resistant gene (Kanr) region, and 3) 3' barcode region and 3' chromosome homology region. To prepare a deletion cassette by combining those three fragments, linking oligos having the nucleotide sequence necessary to combine them together were placed in the overlapped sites. At this time, the length of the chromosome homology region which is the most important factor that determines the efficiency in strain production was determined to be 250 bp. For the 5' chromosome homology region, the sequence of 250 bp long from ATG, the protein coding start codon, toward the direction of the promoter was cut from the chromosome. For the 3' chromosome homology region, the sequence of 250 bp long from TGA, TAG, or TAA, the protein coding stop codon, toward the direction of poly-A was cut from the chromosome.

The nucleotide sequences of these 250 bp long 5' and 3' chromosome homology regions are not presented herein because they are different in each gene and can be presumed easily by those who have knowledge of general genetic information.

The oligos were arranged without gap among them, so that the 2-stranded deletion cassette DNA fragment having nick resulted from the overlapping of oilgos was prepared. Tm values of all oligos were calculated by SantaLucia formula, which would be 60±3° C. (SantaLucia PNAS. 95:1460-5). At both ends of the deletion cassette, comparatively short oligos in 12~16 bp were arranged to make the deletion cassette have blunt ends. Next, all the nicks of all oligos that had been overlapped were ligated by treating a ligase. As a result, the 2-stranded deletion cassette DNA fragment was prepared.

<1-2> Transformation of Deletion Cassette and Confirmation of Gene Targeting Strain To introduce the deletion cassette prepared in Example <1-1> in the diploid fission yeast SP286 strain (ade6-M210/ade6-M216, ura4-D18/ura4-D18, leu1-32/leu1-32), transformation was performed by using lithium acetate method (Moreno et al., Methods Enzymol. 194:795-823). The transformed strain was smeared on YES solid agar medium containing G418 antibiotics (200 mg/l), followed by culture at 30° C. for 3~4 days until colony formation was confirmed. Colony PCR was performed in order to confirm whether or not the transformed colony was completed with the wanted gene targeted. A small amount of cells were taken from the rim of the transformed colony cultured on the solid medium above, which were suspended in triple distilled water. Some of them were taken and proceeded to PCR by using the oligo primer set for strain identification. 5' colony PCR was performed with the 5' region of the chromosome inserted with the deletion cassette by using CP5 and CPN1 or CPN10 oligo primer set. In the meantime, 3' colony PCR was performed with the 3' region of the chromosome by using CP3 and CPC1 or CPC3 oligo primer set. CP5 and CP3 were located in 100~200 bp outside of the chromosome homology region, while CPN1 and CPC1 were located in 200 bp inside toward KanMX4 gene. CPN10 and CPC3 were located in 300 bp inside toward KanMX4 gene in the chromosome. Therefore, the size of the DNA fragment produced from colony PCR was 300~400 bp+80~450 bp (chromosome homology region), so that it would be 500~1,000 bp altogether. Conditions for colony PCR were the same as described in Korean Patent No. 10-0475645, so they are not presented herein.

The oligo nucleotide sequences of CP5 and CP3 are not presented herein because they are different in each gene and can be presumed easily by those who have knowledge of general genetic information. The oligo nucleotide sequences of CPN1, CPN10, CPC1, and CPC3 in kanamycin resistant gene and SEQ. ID. NOs: are presented in Table 1.

TABLE 1

Oligo nucleotide sequences of CPN1, CPN10, CPC1, and CPC3

| Oligo name | Nucleotide sequence | SEQ. ID. NO: |
|---|---|---|
| CPN1 | 5'-CGTCTGTGAGGGGAGCGTTT-3' | 1 |
| CPN10 | 5'-GATGTGAGAACTGTATCCTAGCAAG-3' | 2 |
| CPC1 | 5'-TGATTTTGATGACGAGCGTAAT-3' | 3 |
| CPC3 | 5'-GGCTGGCCTGTTGAACAAGTCTGGA-3' | 4 |

<1-3> Sequencing of Gene Specific Barcode Sequence and PCR Amplification of the Barcode The gene specific barcode is necessary for the systematic confirmation of the strain by using a microarray chip. As described in the above, two gene specific 20 bp long barcodes were inserted in 5' and 3' ends, one on each, in the course of preparation of the gene targeting deletion cassette. Sanger Institute (England) possessing genomic information database notified that the total number of genes in fission yeast is 4,988. So, two barcodes were given to each gene of 4,988, making the total barcode number 9,976. The name of each barcode assigned to each gene was determined by adding the name of extension of _UP or _DN to the systematic nomenclature of the gene. For example, the 5' up-tag barcode of SPAC1002.09c gene was named SPAC1002.09c_UP and the 3' down-tag barcode of SPAC1002.09c was named SPAC1002.09c_DN. The barcode nucleotide sequences were artificial sequences that do not exist on the chromosome of fission yeast, which were determined via computer algorithm in order for the sequences to have Tm value of 60±1° C.

EXAMPLE 2

Selection of Drug and Determination of Dose

<2-1> Selection of Chemicals

To select drugs useable for the present invention, the drugs suitable for the heterozygous strain growth inhibition test were first selected from the chemical list.

Particularly, 110 usable drugs were listed first. Then, solubility of the drug selected through Drugbank database was investigated (C. Knox, V. Law, T. Jewison et al., Nucl. Acids Res., 39 (2011), D1035-D1041). The dose of the selected drug, and the type and the volume of solvent such as water, ethanol, and DMSO to make high concentration stock solution were determined. Next, 75 drugs that had been used more than once as a target drug for the genome-wide chemical genomics of Saccharomyces cerevisiae (S. cerevisiae) were selected (G. Giaever, P. Flaherty, J. Kumm et al., Proc. Natl. Acad. Sci. USA, 101 (2004), 793-798; A. B. Parsons, A. Lopez, I. E. Givoni et al., Cell, 126 (2006), 611-625; G. Giaever, A. M. Chu, L. Ni et al., Nature, 418 (2002), 387-391).

<2-2> Determination of Drug Dose

To determine the proper doses of the 75 drugs selected in this invention that can inhibit particularly the growth of Schizosaccharomyces pombe (S. pombe), the target strain of the invention, the present inventors investigated pool fitness (PF) based on the pool growth inhibition by the conventional method well known to those in the art (P. Y. Lum, C. D. Armour, S. B. Stepaniants et al., Cell, 116 (2004), 121-137; Korean Patent No. 10-0475645).

Particularly, the heterozygous deletion strain of S. pombe (Korean Patent No. 10-1098032) prepared in Example <1-1> was inoculated in a 48-well plate, followed by subculture at 25° C. at 1200 rpm by using Deep Well Maximizer (BNMBR-022UP, Bionex). Total 10 generations were subcultured for 48 hours. Each drug selected above was diluted by 5 times serial-dilution, which was then treated to the cultured strain at the concentration of $5.0 \times 10^{-5}$ M~$1.0 \times 10^{-9}$ M, followed by culture. The 48 well plate containing the cultured strain was centrifuged and the resultant pellet of each well was measured. After determining the effective dose range of each drug, the drug was diluted again by doubling dilution in the above effective dose range. Secondary culture of the S. pombe heterozygous deletion strain was performed by the same manner as described above. Upon completion of the culture, $OD_{600}$ was measured to examine the growth of the strain. PF was calculated by the below mathematical formula 1 according to the concentration of the treated drug. As a result, the concentration of drug that displays 0.85<PF<0.95 was determined as the proper dose of the drug.

$$PF = 1 + \left( \frac{\log\left(\frac{OD_{600}^{treated}}{OD_{600}^{untreated}}\right)}{\log(2) \times g} \right) \quad [\text{Mathematical Formula 1}]$$

In the mathematical formula 1, $OD_{600}$ indicates the optical density of the culture medium measured at 600 nm; and g indicates the generation of the group not-treated with the drug whose optical density was measured also at 600 nm.

As a result, as shown in FIG. 1 and Table 2, the dose of the drug that could efficiently inhibit the growth of the strain was determined. And, total 47 drugs, as listed in Table 2, that demonstrated efficient growth inhibition effect with presenting 0.85<PF<0.95 were selected (FIG. 1 and Table 2).

<2-3> Confirmation of Pool Fitness of S. pombe Heterozygous Deletion Strain According to the Treatment of Selected Drug To confirm the growth inhibition effect of the drug in pool of the S. pombe heterozygous deletion strain quantitatively, the following experiment examining pooled growth was performed according to the conventional method well informed to those in the art (S. E. Pierce, E. L. Fung, D. F. Jaramillo, et al., Nat. Methods 3 (2006) 601-603).

Figure 2:
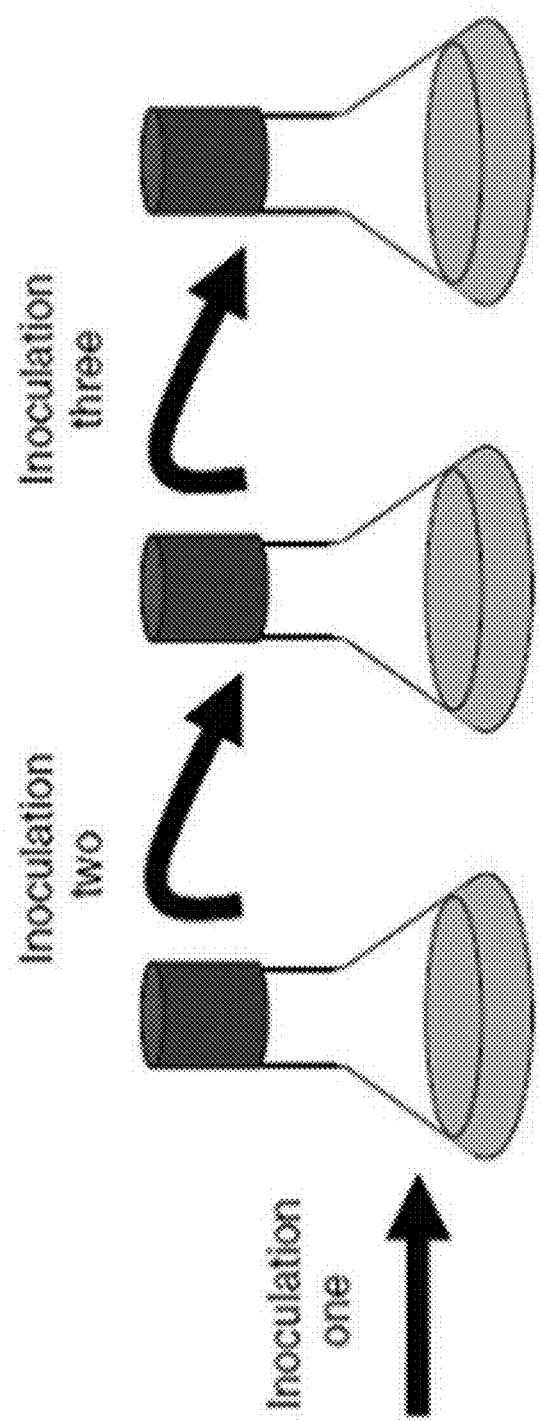
FIG. 2 is a schematic diagram illustrating the pooled growth of the heterozygous deletion strain sub-cultured.

Particularly, 50 ml of culture medium was loaded in each of 54 flasks, to which the drugs selected in Example <2-2> were treated at the doses listed in Table 2. The *S. pombe* heterozygous deletion strain was cultured, followed by sub-culture for total 20 generations at 25° C., and the samples were collected thereby (FIG. 2). In the course of 10 generation sub-culture and 20 generation sub-culture, $OD_{600}$ was measured to confirm the doubling time. Then, pool fitness by doubling time (PFDT) was calculated by the below mathematical formula 2. Sampling error was calculated by counting the difference in generations between the expected generation (ExpG, 20 generations) and the sampled generation (ObsG, 17.5~20.5 generations).

$PF_{DT}$=doubling time of the pool not-treated with the drug/doubling time of the pool treated with the drug    [Mathematical Formula 2]

TABLE 2

Name of the drug selected in this invention, dose thereof, and pool fitness ($PF_{DT}$)

| PrepID*[1] | Drug ID | Name of the drug | Dose(M) | PF1DT*[2] | PF2DT*[3] |
|---|---|---|---|---|---|
| 1 | Ta.1 | Tact | NA | NA | NA |
| 2 | Ta.2 | Tact | NA | NA | NA |
| 3 | D.1 | DMSO(0.5%) | NA | 1.000 | 1.000 |
| 4 | D.2 | DMSO(1.2%) | NA | 0.967 | 0.998 |
| 5 | D.3 | DMSO(3.4%) | NA | 0.914 | 0.943 |
| 6 | 2 | Actinomycin D | 1.00E-06 | 0.650 | 0.709 |
| 7 | 8 | Brefeldin A | 5.00E-05 | 0.973 | 0.986 |
| 8 | 9 | Camptothecin | 3.32E-05 | 0.903 | 0.962 |
| 9 | 11 | Chlorpromazine | 1.25E-04 | 0.892 | 0.975 |
| 10 | 12 | Cimetidine | 7.07E-04 | 0.967 | 0.933 |
| 11 | 14 | Clomipramine hydrochloride | 1.25E-04 | 0.818 | 0.852 |
| 12 | 15 | Clotrimazole | 1.00E-07 | 0.936 | 0.898 |
| 13 | 16 | Cycloheximide | 6.25E-06 | 0.907 | 0.954 |
| 14 | 17 | Cytochalasin B | 3.00E-04 | 0.954 | 0.785 |
| 15 | 19 | Desipramine hydrochloride | 2.50E-04 | 0.879 | 0.937 |
| 16 | 20 | Dilitiazem hydrochloride | 7.07E-04 | 0.896 | 0.890 |
| 17 | 21 | Diphenhydramine hydrochloride | 4.00E-04 | 0.979 | 0.966 |
| 18 | 22 | Dipyridamole | 6.25E-05 | 0.758 | 0.820 |
| 19 | 23 | Doxorubicin | 2.40E-05 | 0.919 | 0.951 |
| 20 | 25 | Dyclonine | 6.80E-05 | 0.742 | 0.809 |
| 21 | 26 | Erythromycin | 2.50E-04 | 0.847 | 0.781 |
| 22 | 28 | 5-Fluorouracil | 2.50E-04 | 0.965 | 0.969 |
| 23 | 29 | Fluoxetine hydrochloride (Prozac) | 8.80E-05 | 0.917 | 0.920 |
| 24 | 31 | Fluvastatin sodium salt | 8.00E-06 | 0.927 | 0.863 |
| 25 | 32 | Gemfibrozil | 1.25E-04 | 0.893 | 0.881 |
| 26 | 34 | Haloperidol | 8.84E-05 | 0.858 | 0.827 |
| 27 | 35 | Hydrocortisone | 1.77E-04 | 0.958 | 1.006 |
| 28 | 37 | Imipramine hydrochloride | 3.54E-04 | 0.901 | 0.892 |
| 29 | 38 | Indomethacin | 1.77E-04 | 0.831 | 0.929 |
| 30 | 43 | Methotrexate | 5.00E-04 | 0.943 | 1.012 |
| 31 | 45 | Metoclopramide hydrochloride | 5.00E-04 | 0.923 | 0.960 |
| 32 | 46 | Minoxidil | 5.00E-04 | 0.894 | 0.878 |
| 33 | 47 | Mitomycin C | 8.00E-05 | 0.840 | 0.756 |
| 34 | 51 | Nicardipine hydrochloride | 2.50E-04 | 0.924 | 0.870 |
| 35 | 52 | Nifedipine | 5.00E-04 | 0.929 | 0.970 |
| 36 | 53 | Nitrofurantoin | 1.77E-04 | 0.890 | 0.940 |
| 37 | 54 | Oligomycin | 4.00E-05 | NA | NA |
| 38 | 55 | Omeprazole | 8.84E-05 | 0.988 | 0.987 |
| 39 | 56 | Paromomycin sulfate | 2.50E-04 | 0.894 | 0.890 |
| 40 | 57 | Phenylbutazone | 6.00E-04 | 0.963 | 0.879 |
| 41 | 58 | Pramoxine hydrochloride | 1.77E-04 | 0.928 | 0.906 |
| 42 | 59 | Pravastatin sodium salt | 1.00E-03 | 0.967 | 0.984 |
| 43 | 60 | Procaine hydrochloride | 2.00E-03 | 0.988 | 0.970 |
| 44 | 61 | Progesterone | 2.00E-05 | 0.963 | 0.979 |
| 45 | 62 | Promethazine hydrochloride | 6.00E-04 | 0.921 | 0.867 |
| 46 | 64 | Sulfamethoxazole | 1.77E-04 | 0.913 | 0.925 |
| 47 | 65 | Sulfinpyrazone | 4.00E-04 | 0.957 | 0.960 |
| 48 | 66 | Tamoxifen | 4.00E-06 | 0.985 | 0.950 |
| 49 | 67.1 | Terbinafine | 3.00E-08 | 0.950 | 0.888 |
| 50 | 67.2 | Terbinafine | 1.50E-08 | 1.024 | 1.085 |
| 51 | 69 | Theophylline anhydrous | 6.50E-04 | 0.887 | 0.924 |
| 52 | 71.1 | Tunicamycin | 3.13E-08 | 0.935 | 1.027 |
| 53 | 71.2 | Tunicamycin | 1.50E-08 | 0.954 | 1.007 |
| 54 | 72 | Valproic acid sodium salt | 2.50E-04 | 0.896 | 0.972 |

PrepID*[1]: test number for the genomic DNA obtained from each pool and DNA chip array;
$PF1_{DT}$*[2]: $PF_{DT}$ of the sample obtained from 10 generation subculture; and
$PF2_{DT}$*[3]: $PF_{DT}$ of the sample obtained from 20 generation subculture.

Figure 3:
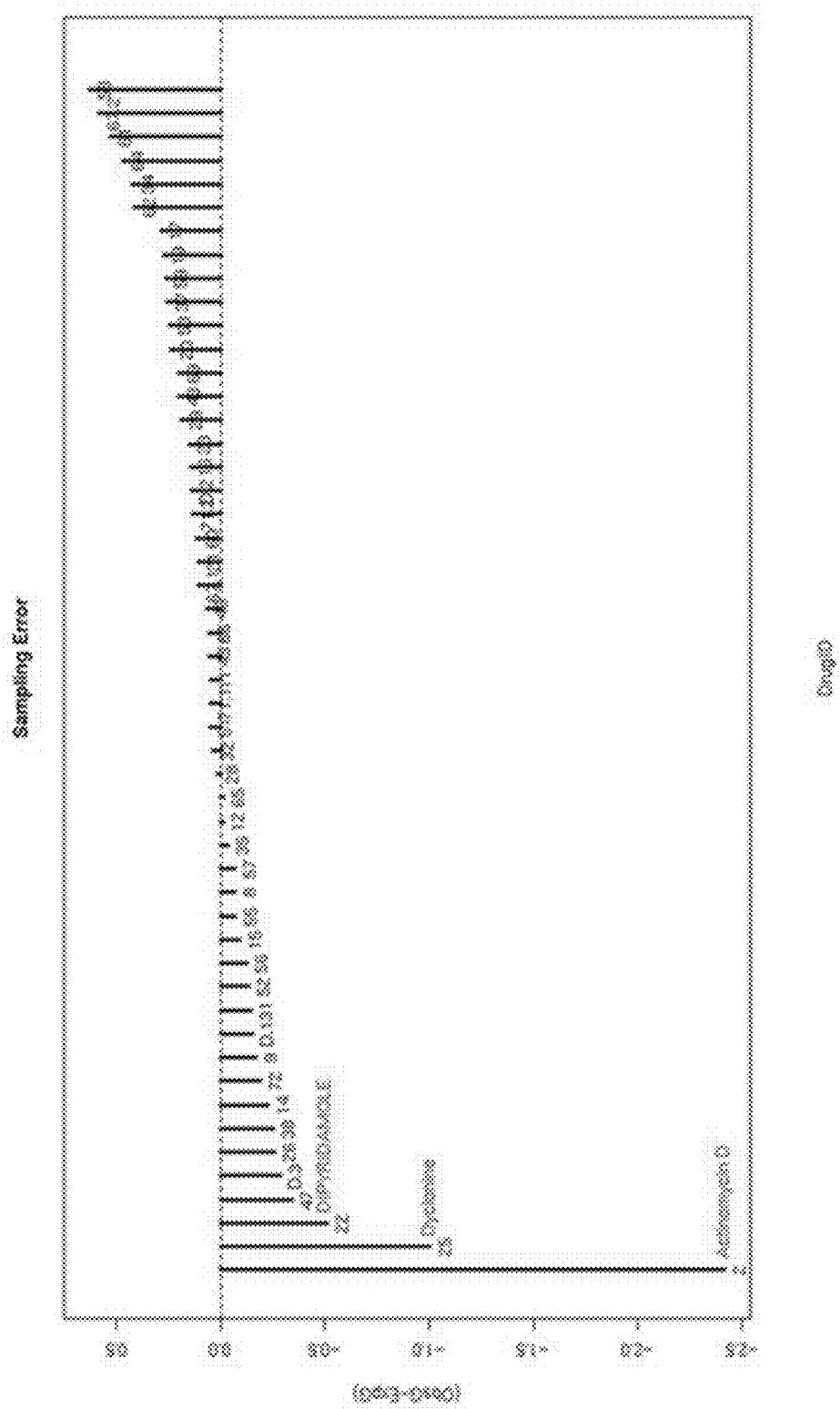
FIG. 3 is a diagram illustrating the sampling error of the *S. pombe* heterozygous deletion strain library sub-cultured for 20 passages.
Figure 4:
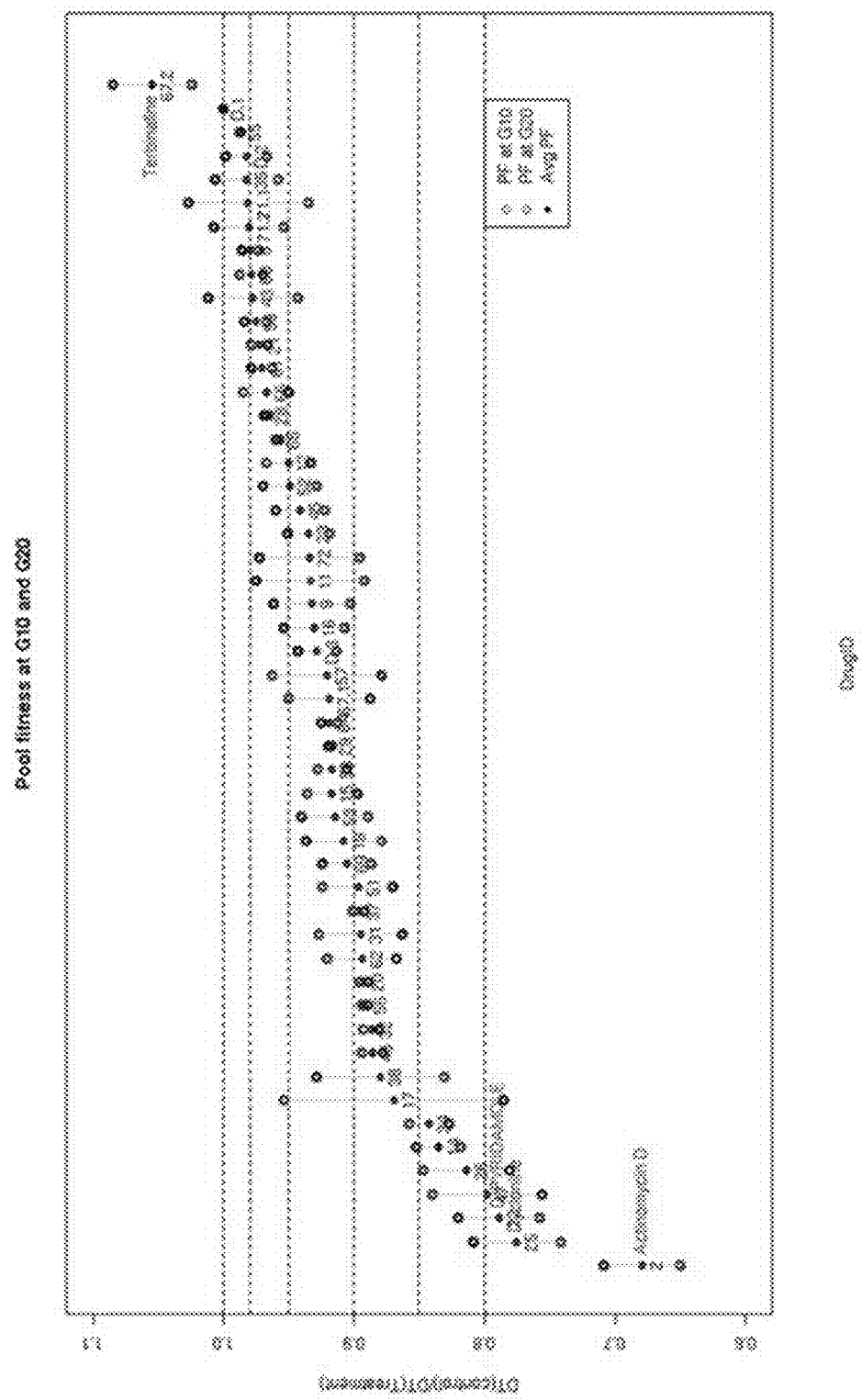
FIG. 4 is a diagram illustrating the pool fitness by doubling time (PFDT) after the 10-passage or 20-passage sub-culture.

As a result, as shown in Table 2, FIG. 3, and FIG. 4, sampling errors were confirmed among actinomycin, dyclonin, and dipyridamole, suggesting that these drugs had the growth inhibition effect on the strain (FIG. 3). It was also confirmed that when $PF_{DT}$ of the sample obtained from 10-generation or 20-generation subculture was examined, the doubling time of the strain pool was 5~30% reduced by the treatment of the drug (Table 2 and FIG. 4).

EXAMPLE 3

Preparation of *S. pombe* Compendium

<3-1> Quantitative Confirmation of the Growth of *S. pombe* Heterozygous Deletion Strain Pool To make the genetic compendium of *S. pombe* heterozygous deletion strain pool, DNA was separated from the strain by the conventional method, followed by chip-hybridization to quantify the growth of the strain (S. E. Pierce, E. L. Fung, D. F. Jaramillo, et al., Nat. Methods 3 (2006) 601-603).

Particularly, genomic DNA was separated from the *S. pombe* heterozygous deletion strain pool obtained after 20 generation-subculture in Example <2-3>. Then, a short DNA barcode sequence in 20 bp long (named "TAG") was inserted in the complementary region of the genomic DNA, followed by amplification with universal primers for the flanking sequence. The amount of the amplified TAG was judged by the growth of each strain, which was quantified by using the DNA chip (Affymetrix, USA) constructed with the complementary sequence of TAG.

The result of the quantitative DNA chip array was not modified by background correction, normalization, or perfect match (PM) and the mean value was used as raw intensity ($I_{raw}$). The parameter for preprocessing the raw intensity was calculated by DNA chip array according to the conventional method informed to those in the art. To calculate the minimum value of the comparative fitness by saturated intensity, modification was performed according to the below mathematical formula 3. The normalized constant was applied to each analysis based on the modified raw intensity. For the modification, chip array was repeated 5 times with the glycerol stock deletion strain pool and the mean value was obtained. The normalized final intensity was log 2-transformed for after analysis.

$$I_{corrected} = I_{raw} \times \exp(-I_{raw}\alpha) \quad \text{[Mathematical Formula 3]}$$

In the mathematical formula 3, '$I_{corrected}$' indicates the modified intensity; '$I_{raw}$' indicates the raw intensity; and '$\alpha$' indicates the variable of modification function calculated with UPTAG and DNATAG which are 0.0003412759 and 0.0002767581 respectively.

<3-2> Calculation of Fitness Score of *S. pombe* Heterozygous Deletion Strain

Error model was calculated according to the conventional method in order to calculate the fitness score of the drug treated *S. pombe* heterozygous deletion strain.

Particularly, low 30% of TAG that displayed a weak intensity and had 4 times as low as the mean value of the intensity of the negative control without TAG in the chip array with 54 chips performed in Example <3-1> was excluded. The compendium of the drug competitive growth experiment was used as the reference set. The reference set herein was confirmed as matrix P composed of the row of strains of 1 . . . i . . . N and the line of drugs of 1 . . . j . . . M. The average and variable of the reference set of each strain were calculated by the below mathematical formula 4. Top 5% TAG intensity and low 10% TAG intensity demonstrated the decreased drug-specific effect, which were therefore excluded.

Z-scores and p-values of the 4400 heterozygous deletion strains were obtained with 47 drugs. The amount of each strain was represented by UPTAG and DNTAG inserted in the upstream and the downstream of the gene that had been eliminated from each strain. To investigate the significance of p-value presenting the detect of the growth in the drug treated strain, the expected intensity of UPTAG and DNTAG in the strain was calculated by the mathematical formula 5. From the mean value thereof, Z-score presenting the statistical distance was obtained. The obtained Z-score was applied to error function or standard normal distribution according to the mathematical formula 6, and the growth detect of each strain was judged by p-value in the range of 0~1.

$$Avg_{i,ref} = \frac{1}{M} \sum_{j}^{M} P_{ij}, \quad \text{[Mathematical Formula 4]}$$

$$Var_{i,ref} = \frac{1}{M-1} \sum_{j}^{M} (P_{ij} - Avg_{i,ref})^2$$

In the mathematical formula 4, i indicates the index of each strain; j indicates the index of each drug; and reference set (ref) indicates all the data set crossing drug j through strain i.

$$Diff_{ij,uptag\,or\,dntag} = P_{ij,uptag\,or\,dntag} - Avg_{ij,ref\,of\,uptag\,or\,ref\,of\,dntag} \quad \text{[Mathematical Formula 5]}$$

$$Diff_{ij,combinded} = \frac{W_{i,uptag} \times Diff_{ij,uptag} + W_{i,dntag} \times Diff_{ij,dntag}}{W_{i,uptag} + W_{i,dntag}}$$

$$W_{i,uptag\,or\,dntag} = \frac{1}{Var_{i,ref}}$$

$$W_{i,combined} = \frac{1}{W_{i,uptag} + W_{i,dntag}}$$

$$Z(score)_{ij} = \frac{Diff_{ij,combined}}{\sqrt{Var_{i,combined}}}$$

In the mathematical formula 5, i indicates the index of each strain; j indicates the index of each drug; and reference set (ref) indicates all the data set crossing drug j through strain i.

$$\text{erfc}\left(x = \frac{z}{\sqrt{2}}\right) = 1 - \text{erf}(x) = \frac{2}{\sqrt{\pi}} \int_{x}^{\infty} e^{-t^2} dt \quad \text{[Mathematical Formula 6]}$$

As a result, Z-scores and p-values of the 4400 heterozygous deletion strains treated with 47 drugs were obtained, from which the '*S. pombe* compendium' of the invention was established.

EXPERIMENTAL EXAMPLE 1

Screening of Direct Drug Target Protein Using Drug-induced Haploinsufficiency Profile (DI-HI)

To screen a protein and a gene targeted directly by a specific drug using *S. pombe* compendium, drug-induced haploinsufficiency (DI-HI) profiling was performed.

Particularly, the *S. pombe* heterozygous deletion strain was cultured either in the presence or absence of the 47 drugs selected in Example 2. DNA chip array was performed by the method described in Example 3, and the growth defect of the cultured *S. pombe* genome-wide heterozygous deletion strain was confirmed quantitatively. The growth defect by the presence or absence of each drug was investigated by the method illustrated in the schematic diagram of FIG. 5 to judge whether the heterozygous deletion gene was haplo-insufficient (HI) or haplo-sufficient (HS).

When the strain displaying a significant growth defect by the treatment of a specific drug was confirmed to have the heterozygous deletion mutant gene (genes C and D of FIG. 5A), if a related homozygous deletion strain displayed a significant growth detect or even experienced death (gene C of FIG. 5B), the heterozygous deletion strain sensitive to the treated drug would be judged to have growth defect directly by the treated drug. On the other hand, if a gene induced growth defect in the heterozygous deletion strain but did not induce growth defect in the homozygous deletion strain, it was judged that the growth defect was attributed to the indirect drug effect of the gene like the multi-drug sensitive gene.

Figure 5:
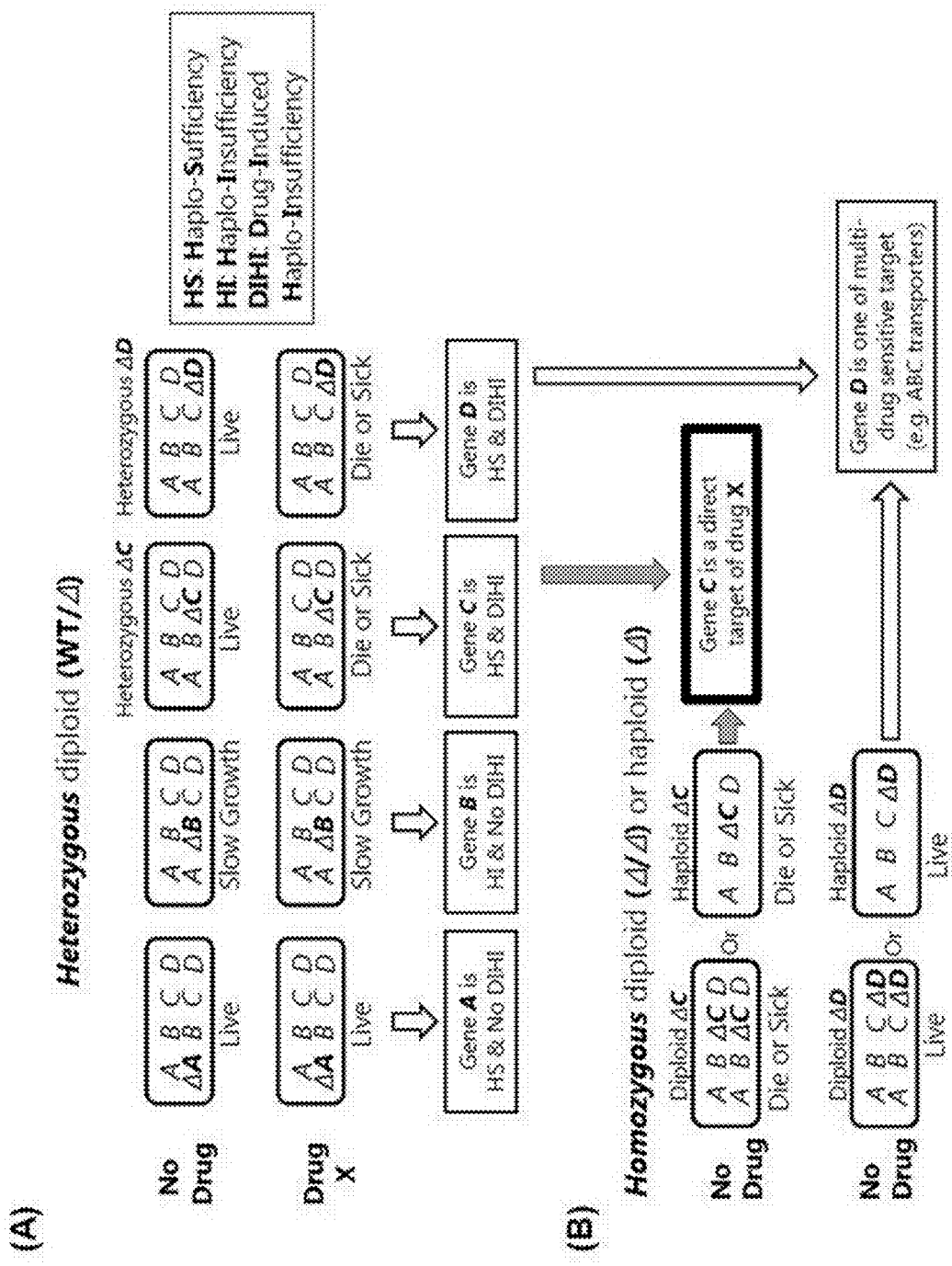
FIG. 5 is a schematic diagram illustrating the selection process of a drug target gene through the drug-induced haploinsufficiency profile obtained from *S. pombe*.

As a result, as shown in FIG. 5, most of the genes in *S. pombe* were HS (gene A of FIG. 5A), and only less than 3% of the genes (gene B) were HI in the aspect of cell growth (FIG. 5).

EXPERIMENTAL EXAMPLE 2

Screening of Direct Drug Target Protein Using Evolutionarily Conserved Drug Targets (ecDTs)

The analysis of bioactive compounds through the screening of *S. pombe* DIHI profiles is limited in screening drug target proteins directly in various living things. So, ecDT was screened herein with comparing both compendiums of S. pombe and S. cerevisiae.

Particularly, the S. pombe heterozygous deletion strain was cultured either in the presence or absence of the 47 drugs selected in Example 2. DNA chip array was performed by the same manner as described in Example 3. The cultured S. pombe genome-wide heterozygous deletion strain was quantified to investigate the growth defect therein The growth defect of the cultured S. pombe genome-wide heterozygous deletion strain was confirmed quantitatively, and the compendium was made with the results. Then, those drugs that had been confirmed to show the hypersensitive gene having p-value of less than 0.0001 against S. pombe, which were 36 drugs in total, were selected from the DIHI profiles of Experimental Example 1. S. pombe compendium was compared with S. cerevisiae compendium according to the treatment of the selected drugs. Then, the orthologous genes between S. pombe and S. cerevisiae were mapped according to the schematic diagrams shown in FIG. 6 and FIG. 7. When the confirmed genes were all potential drug target genes (DT), the genes were named ecDT and selected. 13 drugs presumed to target the ecDT were selected. In the meantime, the genes confirmed as DT only in one of those strains, S. pombe and S. cerevisiae, were defined as evolutionarily diverged DT (edDT). Among the ecDTs, non-essential genes, multi-drug sensitive genes, and less conserved genes in eukaryotes were eliminated and the remaining ecDTs were selected as target drugs.

Figure 6:
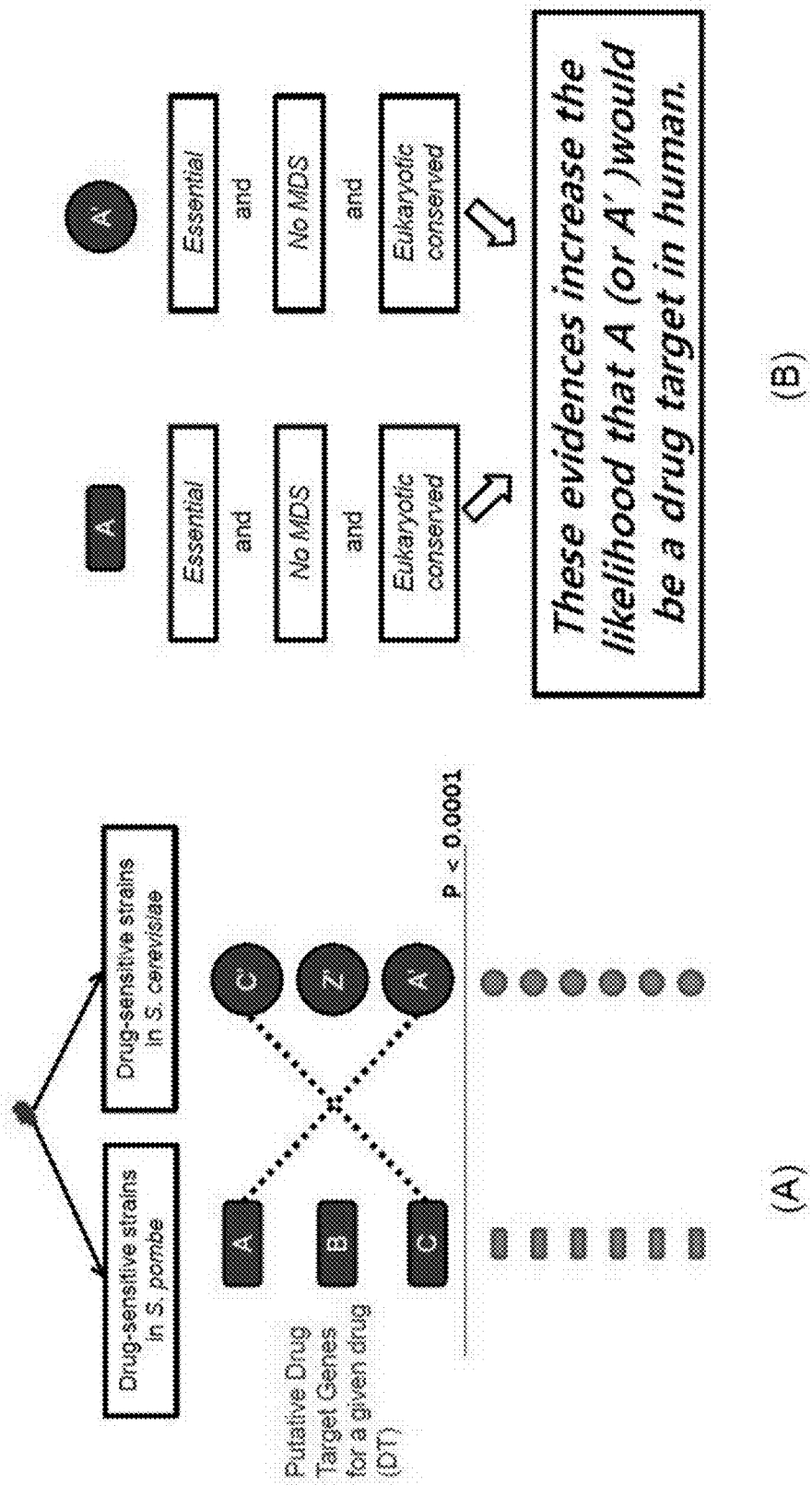
FIG. 6 is a schematic diagram illustrating the selection process of evolutionarily conserved drug targets (ecDTs) by comparing the chemical-genetic profile compendiums of *S. pombe* with those of *S. cerevisiae*.

As a result, as shown in FIG. 6~FIG. 9, and Table 3~Table 6, 9 drugs confirmed to have direct effect on both S. pombe and S. cerevisiae were selected (FIGS. 6 and 7). The ecDT percentages of the selected drug were 7.41% in S. pombe and 2.78% in S. cerevisiae, that is both were less than 10%. On the other hand, the percentages of the orthologous genes selected by edDT were 92.59% in S. pombe and 97.22% in S. cerevisiae, suggesting that more than 90% of the orthologous genes were sensitive to one of these two strains in the presence of same drugs (Table 3 and Table 6).

Figure 8:
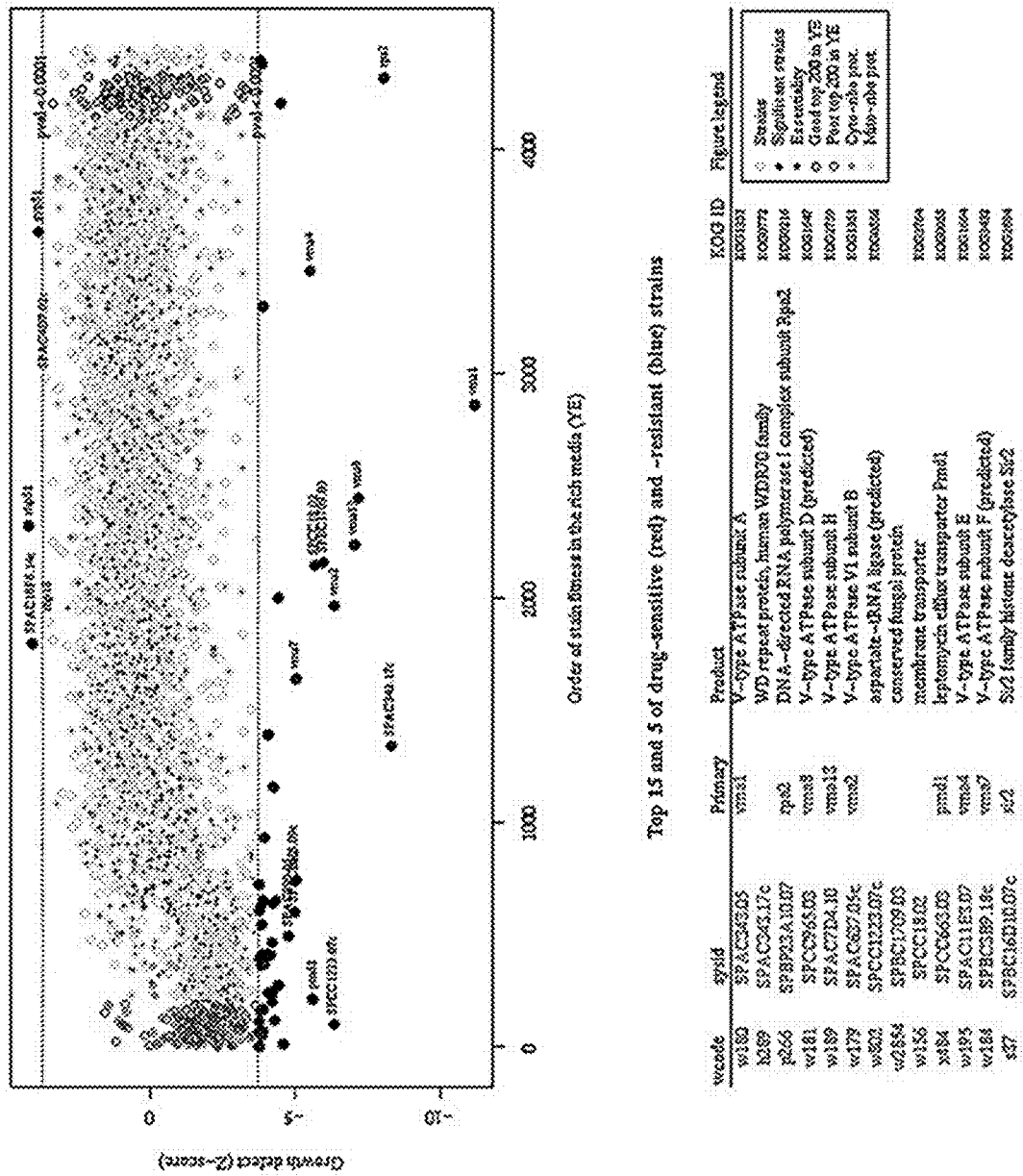
FIG. 8 is a diagram illustrating the doxorubicin-sensitive gene selected from the *S. pombe* compendiums.
Figure 9:
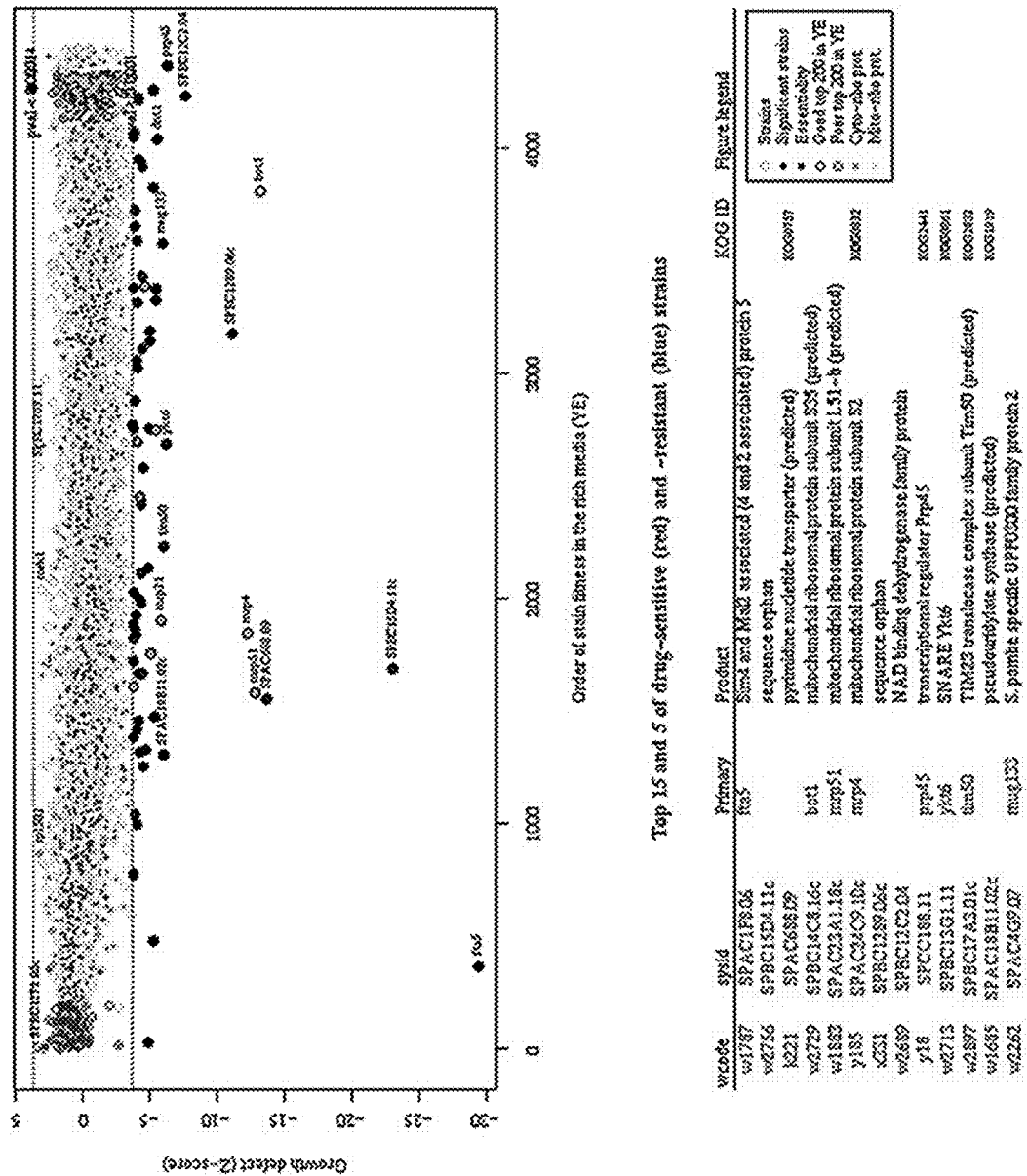
FIG. 9 is a diagram illustrating the erythromycin-sensitive gene selected from the *S. pombe* compendiums.

Particularly, ERG1 of terbinafine, ALG7 of Tunicamycin, and ERG11 of clotrimazole were confirmed as ecDTs which were the primary direct target proteins (Table 5). In the meantime, ecDTs of doxorubicin, mitomycin C, methotrexate, dyclonine, haloperidol, and erythromycin were not fit for the primary tentative target pathway, so that they were presumed to be more involved in the secondary drug effect through eukaryotic conservation in human cells (Table 6). The target genes that were sensitive directly to the used drugs were identified from the whole length of the genome of S. pombe strain by confirming the direct target gene (ecDT) sets of the said 9 drugs (FIGS. 8 and 9).

TABLE 3

Comparative statistics of tentative drug target genes

| | S. pombe | | | S. cerevisiae | | |
|---|---|---|---|---|---|---|
| | Conserved | Diverged | No Ortholog | Conserved | Diverged | No Ortholog |
| 5-Fluorouracil | 2 | 12 | 2 | 2 | 316 | 143 |
| Actinomycin D | 42 | 334 | 113 | 41 | 340 | 196 |
| Clotrimazole | 11 | 50 | 16 | 11 | 342 | 185 |
| Doxorubicin | 4 | 25 | 9 | 4 | 293 | 143 |
| Dyclonine | 11 | 53 | 18 | 10 | 331 | 144 |
| Erythromycin | 1 | 46 | 11 | 1 | 25 | 16 |
| Haloperidol | 6 | 85 | 30 | 6 | 113 | 46 |
| Methotrexate | 4 | 9 | 3 | 4 | 1218 | 603 |
| Mitomycin C | 7 | 133 | 34 | 8 | 173 | 70 |
| Phenylbutazone | 1 | 174 | 79 | 1 | 0 | 0 |
| Progesterone | 1 | 30 | 6 | 1 | 39 | 17 |
| Terbinafine | 4 | 223 | 72 | 4 | 51 | 23 |
| Tunicamycin | 2 | 26 | 11 | 2 | 77 | 48 |
| Total | 96 | 1200 | 404 | 95 | 3318 | 1634 |
| | 7.41% | 92.59% | | 2.78% | 97.22% | |

TABLE 4

Ortholog mappings of evolutionarily conserved drug target genes

| drug | S. Pombe | S. cerevisiae |
|---|---|---|
| 5-Fluorouracil | SPAC637.05c | YBR127C |
| 5-Fluorouracil | SPAC664.06 | YNL002c |
| Actinomycin D | SPAC11D3.08c | YKL174C |
| Actinomycin D | SPAC13C5.02 | YPR152c |
| Actinomycin D | SPAC144.18 | YER039C |
| Actinomycin D | SPAC17G6.10 | YFR037c |
| Actinomycin D | SPAC17G8.10c | YHR115C |
| Actinomycin D | SPAC20G4.04c | YLR288C |
| Actinomycin D | SPAC22A12.04c | YLR367W |
| Actinomycin D | SPAC23C4.12 | YPL204W |
| Actinomycin D | SPAC25B8.09 | YHR209W |
| Actinomycin D | SPAC26F1.09 | YMR192W |
| Actinomycin D | SPAC26F1.10c | YER075C |
| Actinomycin D | SPAC4H3.08 | YKR009c |
| Actinomycin D | SPAC57A10.05c | YIL046W |
| Actinomycin D | SPAC644.04 | YPL228W |
| Actinomycin D | SPAC6F12.15c | YKL022C |
| Actinomycin D | SPAC8F11.09c | YLR285W |
| Actinomycin D | SPAC9E9.12c | YGR281W |
| Actinomycin D | SPBC106.07c | YGR147C |
| Actinomycin D | SPBC1604.14c | YHL007C |
| Actinomycin D | SPBC16A3.04 | YIL093c |
| Actinomycin D | SPBC16E9.01c | YKL109W |
| Actinomycin D | SPBC1703.12 | YBL067C |
| Actinomycin D | SPBC17A3.01c | YPL063W |
| Actinomycin D | SPBC18A7.02c | YKL039W |
| Actinomycin D | SPBC21D10.07 | YKL137W |
| Actinomycin D | SPBC25B2.03 | YMR140W |
| Actinomycin D | SPBC2D10.04 | YKR021W |
| Actinomycin D | SPBC36.08c | YGR120C |
| Actinomycin D | SPBC3B9.07c | YOR340C |
| Actinomycin D | SPBC3E7.13c | YGR129W |
| Actinomycin D | SPBC3H7.15 | YPL204W |
| Actinomycin D | SPBC56F2.11 | YNL277W |
| Actinomycin D | SPBC6B1.02 | YIL095W |
| Actinomycin D | SPBC947.15c | YMR145C |

TABLE 4-continued

Ortholog mappings of evolutionarily conserved drug target genes

| drug | S. Pombe | S. cerevisiae |
|---|---|---|
| Actinomycin D | SPCC1223.01 | YDR266c |
| Actinomycin D | SPCC1281.07c | YMR251W |
| Actinomycin D | SPCC1322.08 | YLR248W |
| Actinomycin D | SPCC1393.09c | YDR152W |
| Actinomycin D | SPCC1672.12c | YOR164C |
| Actinomycin D | SPCC548.07c | YDR536W |
| Actinomycin D | SPCC548.07c | YHR094C |
| Actinomycin D | SPCC965.03 | YEL051W |
| Actinomycin D | SPCP1E11.02 | YIL095W |
| Clotrimazole | SPAC12G12.11c | YPL191C |
| Clotrimazole | SPAC13A11.02c | YHR007C |
| Clotrimazole | SPAC1420.02c | YJR064W |
| Clotrimazole | SPAC23C4.12 | YPL204W |
| Clotrimazole | SPAC328.01c | YDR335W |
| Clotrimazole | SPAC458.02c | YOR198C |
| Clotrimazole | SPAC7D4.12c | YJL107C |
| Clotrimazole | SPBC1709.14 | YPL096W |
| Clotrimazole | SPBC725.02 | YDL235c |
| Clotrimazole | SPCC1840.03 | YMR308c |
| Clotrimazole | SPCC18B5.01c | YOR153W |
| Doxorubicin | SPAC343.05 | YDL185W |
| Doxorubicin | SPAC644.14c | YER095W |
| Doxorubicin | SPBC3B9.18c | YGR020C |
| Doxorubicin | SPBP23A10.07 | YPR010c |
| Dyclonine | SPAC17A2.09c | YBR212W |
| Dyclonine | SPAC17H9.04c | YDL167C |
| Dyclonine | SPAC22F8.08 | YIL109C |
| Dyclonine | SPAC29A4.17c | YAL008W |
| Dyclonine | SPAC328.04 | YPL074W |
| Dyclonine | SPBC1652.02 | YBR069C |
| Dyclonine | SPBC16G5.01 | YFR052W |
| Dyclonine | SPBC646.08c | YPL145C |
| Dyclonine | SPBC6B1.10 | YDR364c |
| Dyclonine | SPCC1450.10c | YNL240C |
| Dyclonine | SPCC23B6.01c | YPL145C |
| Erythromycin | SPAC688.09 | YBR192W |
| Haloperidol | SPAC1F8.01 | YGR289C |
| Haloperidol | SPAC25B8.08 | YPR089W |
| Haloperidol | SPAC2F7.17 | YGL143c |
| Haloperidol | SPAC4D7.12c | YLR243W |
| Haloperidol | SPAC767.01c | YKR001C |
| Haloperidol | SPBC27B12.03c | YLR056W |
| Methotrexate | SPAC1751.01c | YEL007W |
| Methotrexate | SPAC56E4.03 | YHR137W |
| Methotrexate | SPACUNK4.12c | YLR389C |
| Methotrexate | SPBC2G2.01c | YAL067C |
| Mitomycin C | SPAC1250.01 | YIL126W |
| Mitomycin C | SPAC23H3.08c | YOR026W |
| Mitomycin C | SPAP8A3.07c | YBR249C |
| Mitomycin C | SPAP8A3.07c | YDR035W |
| Mitomycin C | SPBC1652.02 | YEL063C |
| Mitomycin C | SPBC336.12c | YLR182W |
| Mitomycin C | SPCC1020.02 | YGL093W |
| Mitomycin C | SPCC1840.02c | YLR342W |
| Phenylbutazone | SPAC20G8.04c | YOR356W |
| Progesterone | SPBC36B7.08c | YNL246W |
| Terbinafine | SPAC15F9.01c | YGL060W |
| Terbinafine | SPBC660.10 | YJL102W |
| Terbinafine | SPBC713.12 | YGR175c |
| Terbinafine | SPBC9B6.07 | YDR087c |
| Tunicamycin | SPBC1271.03c | YLR019W |
| Tunicamycin | SPBC15D4.04 | YBR243c |

Actinomycin D[a]: SPAC23C4.12 and SPBC3H7.15 are orthologous to YPL204W;
Dyclonine[b]: SPBC646.08c and SPCC23B6.01c are orthologous to YPL145C; and
Mitomycin C[c]: YBR249C and YDR035W are orthologous to SPAP8A3.07c.

TABLE 5

Target proteins known from the evolutionarily conserved drug target genes in S. pombe and S. cerevisiae

| Gene (Spo) | Gene (Sce) | Ess (Spo) | Ess (Sce) | MDS (Sce) | Conservation | -log (p) (Spo) | -log (p) (Sce) | Dose (µM) (Spo) | Dose (Sce) |
|---|---|---|---|---|---|---|---|---|---|
| Tunicamycin (antibiotics used in glycoprotein research; known target gene: ALG7) | | | | | | | | | |
| gpt2 | ALG7 | ESS | ESS | NO | Euk (Sce: 52% Hs: 43%) | −4.976 | −4.898 | 0.03125 | 0.6 µM |
| gpt2 | ALG7 | ESS | ESS | NO | Euk | −4.976 | −4.216 | 0.03125 | 0.6 µM |
| gpt2 | ALG7 | ESS | ESS | NO | Euk | −4.976 | −5.227 | 0.03125 | 0.015 µM |
| gpt2 | ALG7 | ESS | ESS | NO | Euk | −4.976 | −24 | 0.03125 | 150 ng/mL |
| Terbinafine (antimicrobial; known target gene: ERG1) | | | | | | | | | |
| erg1 | ERG1 | ESS | ESS | NO | Euk (Sce: 38% Hs: 42%) | −49.77 | −8.09 | 0.03 | 7.2 µM |
| erg1 | ERG1 | ESS | ESS | NO | Euk | −24.83 | −8.09 | 0.015 | 7.2 µM |
| | RRP1 | | ESS | NO | Euk (Sce: 37%, Hs: 44%) | −6.1 | −4.515 | 0.03 | 7.2 µM |
| erg1 | ERG1 | ESS | ESS | NO | Euk | −49.77 | −7.619 | 0.03 | 7.2 µM |
| erg1 | ERG1 | ESS | ESS | NO | Euk | −24.83 | −7.619 | 0.015 | 7.2 µM |
| erg1 | ERG1 | ESS | ESS | NO | Euk | −24.83 | −80.59 | 0.015 | 2.5 ug/ml |
| erg1 | ERG1 | ESS | ESS | NO | Euk | −49.77 | −80.59 | 0.03 | 2.5 ug/ml |

TABLE 5-continued

Target proteins known from the evolutionarily
conserved drug target genes in S. pombe and S. cerevisiae

| Gene (Spo) | Gene (Sce) | Ess (Spo) | Ess (Sce) | MDS (Sce) | Conservation | −log (p) (Spo) | −log (p) (Sce) | Dose (μM) (Spo) | Dose (Sce) |
|---|---|---|---|---|---|---|---|---|---|
| | Clotrimazole (antifungal; known target gene: ERG11) |
| erg11 | ERG11 | ESS | ESS | NO | Euk (Sce: 49%, Hs: 39%) | −13.15 | −22.27 | 0.1 | 2 μM |
| erg11 | ERG11 | ESS | ESS | NO | Euk | −13.15 | −19.98 | 0.1 | 2 μM |

Spo: *S. pombe*;
Sce: *S. cerevisiae*;
HS: *Homo sapiense*;
Ess: Essential gene;
MDS: Multi-drug sensitive; and
Euk: Eukaryotic conservation.

TABLE 6

Target proteins confirmed from the evolutionarily
conserved drug target genes in S. pombe and S. cerevisiae Doxorubicin (Antineoplastic)

| Gene (Spo) | Gene (Sce) | Ess (Spo) | Ess (Sce) | MDS (Sce) | Conservation | −log (p) (Spo) | −log (p) (Sce) | Dose (μM) (Spo) | Dose (Sce) |
|---|---|---|---|---|---|---|---|---|---|
| vma7 | VMA7 | ESS | | NO | Euk (Sce: 59%, Hs: 52%) | −6.287 | −28.85 | 24 | 62.5 |
| vma1 | TFP1 | ESS | | NO | Euk (Sce: longer, Hs: 67%) | −28.26 | −8.374 | 24 | 62.5 |
| rpa2 | RPA135 | ESS | ESS | NO | Euk (Sce: 62%, Hs: longer) | −15.09 | −6.279 | 24 | 62.5 |

Mitomycin C (Antineoplastic)

| Gene (Spo) | Gene (Sce) | Ess (Spo) | Ess (Sce) | MDS (Sce) | Conservation | −log (p) (Spo) | −log (p) (Sce) | Dose (μM) (Spo) | Dose (Sce) |
|---|---|---|---|---|---|---|---|---|---|
| spc7 | SPC105 | ESS | ESS | NO | 진균 Fungal | −17.27 | −14.52 | 80 | 1000 |
| snf21 | STH1 | ESS | ESS | NO | Euk | −4.022 | −5.49 | 80 | 1000 |
| cdc10 | SWI6 | ESS | | NO | 진균 | −6.16 | −5.228 | 80 | 1000 |

Methotrexate (Antineoplastic)

| Gene (Spo) | Gene (Sce) | Ess (Spo) | Ess (Sce) | MDS (Sce) | 보존정도 | −log (p) (Spo) | −log (p) (Sce) | Dose (μM) (Spo) | Dose (Sce) |
|---|---|---|---|---|---|---|---|---|---|
| ssr2 | RSC8 | ESS | ESS | NO | Euk | −4.28 | −4.275 | 500 | 250 |

Dyclonine (Local anesthetic)

| Gene (Spo) | Gene (Sce) | Ess (Spo) | Ess (Sce) | MDS (Sce) | Conservation | −log (p) (Spo) | −log (p) (Sce) | Dose (μM) (Spo) | Dose (Sce) |
|---|---|---|---|---|---|---|---|---|---|
| SPCC1450.10c | NAR1 | ESS | ESS | NO | 다양한 종 | −6.928 | −4.84 | 68 | 500 |
| SPAC22F8.08 | SEC24 | ESS | ESS | NO | Euk | −12.19 | −6.632 | 68 | 500 |
| rpn12 | RPN12 | | ESS | NO | Euk | −40.98 | −4.338 | 68 | 500 |

Haloperidol (antipsychotic)

| Gene (Spo) | Gene (Sce) | Ess (Spo) | Ess (Sce) | MDS (Sce) | Conservation | −log (p) (Spo) | −log (p) (Sce) | Dose (μM) (Spo) | Dose (Sce) |
|---|---|---|---|---|---|---|---|---|---|
| fet5 | YLR243W | ESS | ESS | NO | Euk | −4.402 | −7.301 | 88.3 | 125 |

TABLE 6-continued

Target proteins confirmed from the evolutionarily
conserved drug target genes in *S. pombe* and *S. cerevisiae*

Erythromycin (antimicrobial)

| Gene (Spo) | Gene (Sce) | Ess (Spo) | Ess (Sce) | MDS (Sce) | Conservation | −log (p) (Spo) | −log (p) (Sce) | Dose (μM) (Spo) | Dose (Sce) |
|---|---|---|---|---|---|---|---|---|---|
| SPAC688.09 | RIM2 | ESS | ESS | NO | Euk | −42.17 | −4.63 | 250 | 2.5 mg/ml |

Spo: *S. pombe*;
Sce: *S. cerevisiae*;
HS: *Homo sapiense* ;
Ess: Essential gene;
MDS: Multi-drug sensitive; and
Euk: Eukaryotic conservation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A screening method for a drug target gene comprising the following steps:
   i) generating a heterozygous deletion strain library of *Schizosaccharomyces pombe* (*S. pombe*) and a heterozygous deletion strain library of *Saccharomyces cerevisiae* (*S. cerevisiae*), wherein generating each heterozygous deletion strain comprises: preparing a gene targeting heterozygous fission yeast strain using a gene targeting deletion cassette comprising a selection marker gene, gene specific microarray barcode sequences arranged on both sides of the selection marker gene, and homologous recombination sites arranged on both sides of the barcode sequence;
   ii) culturing each of the heterozygous deletion strain library of *Schizosaccharomyces pombe* (*S. pombe*)and the heterozygous deletion strain library of *Saccharomyces cerevisiae* (*S. cerevisiae*);
   iii) treating the cultures of step ii) with a sample drug, followed by further culturing;
   iv) confirming growth of the strain libraries cultured in step iii); and
   v) comparing a compendium of heterozygous deletion genes from the *S. pombe* strain library with a compendium of heterozygous deletion genes from the *S. cerevisiae* strain library, demonstrating inhibition of growth in step iv), wherein the heterozygous deletion genes of the strain libraries are evolutionarily conserved Drug Targets (ecDTs);
   vi) generating a list of orthologous genes from the comparisons of each deletion gene compendium in step v), wherein said orthologous genes induce growth defects in the heterozygous deletion strains but do not induce growth defects in a homozygous deletion strain;
   vii) filtering the list of orthologous genes from step vi) to remove any gene which is:
      a) not an essential gene necessary for survival of the strain;
      b) a gene that shows multi-drug sensitivity (MDS); and
      c) not a eukaryotic conserved gene;
   viii) identifying remaining genes from the list of orthologous genes in step vii) as a drug target gene,
   wherein the drug target gene is selected from the group consisting of vma7, vma1, rpa2, spc7, snf21, cdc10, ssr2, SPCC1450.10c, SPAC22F8.08, rpn12, fet5, and SPAC688.09.

2. The screening method for a drug target gene according to claim 1, wherein the sample drug of step ii) is selected from the group consisting of doxorubicin, dyclonine, erythromycin, haloperidol, methotrexate, and mitomycin C.

3. The screening method for a drug target gene according to claim 1, wherein the measurement of the growth in step iii) is performed by DNA chip array or high-throughput spot assay.

* * * * *